United States Patent
Elomari et al.

(10) Patent No.: US 11,807,610 B2
(45) Date of Patent: Nov. 7, 2023

(54) FUNCTIONALIZED IONIC LIQUID FOR SOLVATING HEAVY AROMATIC COMPOUNDS

(71) Applicant: Chevron U.S.A. Inc., San Ramon, CA (US)

(72) Inventors: Saleh Ali Elomari, Fairfield, CA (US); Huping Luo, Moraga, CA (US); Timi Pravin Singa, Richmond, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 159 days.

(21) Appl. No.: 17/666,663

(22) Filed: Feb. 8, 2022

(65) Prior Publication Data

US 2023/0250061 A1 Aug. 10, 2023

(51) Int. Cl.
*C07D 215/10* (2006.01)

(52) U.S. Cl.
CPC .................. *C07D 215/10* (2013.01)

(58) Field of Classification Search
CPC ............ C07D 215/10; B01D 11/043; B01D 11/0434; B01D 11/0446; B01D 11/0457; B01D 11/0488; B01D 11/0492; C10G 21/28; C10G 25/003; C10G 67/04; C10G 2300/206; C10G 47/00; C10G 21/20; C10G 2300/201
USPC ...................................................... 585/865
See application file for complete search history.

(56) References Cited

U.S. PATENT DOCUMENTS

| | | |
|---|---|---|
| 8,574,426 B2 | 11/2013 | Mezza et al. |
| 10,920,157 B2 | 2/2021 | Koseoglu |
| 10,934,493 B1 | 3/2021 | Elomari et al. |
| 2012/0024756 A1 | 2/2012 | Verma et al. |
| 2014/0001100 A1 | 1/2014 | Abai et al. |

FOREIGN PATENT DOCUMENTS

| | | | | |
|---|---|---|---|---|
| GB | 2485824 A | * | 5/2012 | ........... C07C 211/63 |
| WO | 2021099850 A1 | | 5/2021 | |

OTHER PUBLICATIONS

PCT International Search Report, International application No. PCT/IB2023/050884, dated Mar. 30, 2023.

* cited by examiner

*Primary Examiner* — Prem C Singh
*Assistant Examiner* — Francis C Campanell (57) ABSTRACT

A process for removing heavy polycyclic aromatic contaminants from a hydrocarbon stream using a quinolinium ionic liquid is described. The process includes contacting the hydrocarbon stream comprising the contaminant with a hydrocarbon-immiscible quinolinium ionic liquid to produce a mixture comprising the hydrocarbon and a hydrocarbon-immiscible quinolinium ionic liquid comprising at least a portion of the removed contaminant; and separating the mixture to produce a hydrocarbon effluent having a reduced level of the contaminant and a hydrocarbon-immiscible quinolinium ionic liquid effluent comprising the hydrocarbon-immiscible quinolinium ionic liquid comprising at least the portion of the removed contaminant.

21 Claims, 5 Drawing Sheets

FUNCTIONALIZED IONIC LIQUID FOR SOLVATING HEAVY AROMATIC COMPOUNDS

FIELD

This disclosure relates to a process for reducing the concentration of heavy polycyclic aromatics in a hydrocarbon stream.

BACKGROUND

Hydroprocessing can include processes which convert hydrocarbons in the presence of hydroprocessing catalyst and hydrogen to more valuable products. Hydrocracking is a hydroprocessing process in which hydrocarbons crack in the presence of hydrogen and hydrocracking catalyst to lower molecular weight hydrocarbons.

Heavy polynuclear aromatic (HPNA) compounds may be an undesired secondary product of a hydrocracking process, particularly of high conversion hydrocracking units. Recycling unconverted oil to increase yields of distillate product can result in accumulation of HPNA compounds in the unconverted oil. Accumulated HPNA compounds in the recycle oil may deposit on the catalyst as coke, which may degrade catalyst performance and result in shorter catalyst cycle length. In addition, HPNA compounds can deposit on equipment in the cooler sections of the process unit. Production of HPNA compounds can be more pronounced for hydrocracking units processing heavier feeds. Thus, it would be desirable to remove HPNA compounds from the unconverted oil to minimize catalyst deactivation and equipment fouling.

SUMMARY

In one aspect, there is provided a process for removing a contaminant comprising at least one heavy polynuclear aromatic (HPNA) compound from a hydrocarbon stream, the process comprising: (a) contacting the hydrocarbon stream comprising the contaminant with a lean hydrocarbon-immiscible quinolinium ionic liquid under contacting conditions to produce a mixture comprising the hydrocarbon and a rich hydrocarbon-immiscible quinolinium ionic liquid comprising at least a portion of the removed contaminant; and (b) separating the mixture to produce a hydrocarbon effluent having a reduced level of the contaminant and a rich hydrocarbon-immiscible quinolinium ionic liquid effluent comprising the rich hydrocarbon-immiscible quinolinium ionic liquid comprising at least the portion of the removed contaminant.

DETAILED DESCRIPTION

In this specification, the following words and expressions, if and when used, have the meanings ascribed below.

The term "heavy polynuclear aromatics" may be abbreviated as "HPNA" and is defined as polycyclic aromatic hydrocarbons having at least 4 or even 6 fused aromatic rings, such as benzoperylenes, coronenes, and ovalenes. In general, polynuclear aromatic hydrocarbons described herein are molecules formed strictly of carbon and hydrogen, which do not contain any heteroatoms (i.e., atoms other than carbon or hydrogen).

The term "asphaltenes" refers to a mix of high molecular weight polycyclic aromatic hydrocarbons, which consist primarily of carbon, hydrogen, nitrogen, oxygen and sulfur with trace amounts of metals such as vanadium and nickel, and a hydrogen to carbon ratio of about 1.2 to 1. Operationally, asphaltenes refers to the n-heptane-insoluble, toluene-soluble component of a carbonaceous material. Asphaltenes are the sticky, black, highly viscous residue of distillation processes. Asphaltenes contain highly polar species that tend to associate or aggregate, which has made complete molecular analysis of asphaltenes, for example by mass spectrometry, difficult.

The term "unconverted oil" may be abbreviated herein as "UCO" and can refer to a high boiling hydrocarbon fraction, separated from the hydrocracker effluent, that can boil at temperatures above those representative of diesel boiling range hydrocarbons. Generally, the unconverted oil has a T1 of at least about 250° C., typically at least about 288° C., and often at least about 316° C. In many cases this higher boiling fraction will represent a minor amount (e.g., no more than about 45%, by volume) of the hydrocracker effluent, due to the significant extent of cracking reactions occurring in the hydrocracking reactor or reaction zone to provide lower molecular weight products. The distillation end point of the unconverted oil is generally close to that of the feedstock. When vacuum gas oil (VGO) is used as a major component of, or as the entire, fresh feed component, the unconverted oil typically has a T99 of no more than about 593° C. (e.g., in the range of about 510° C. to about 593° C.), and often at most about 566° C. When deasphalted oil (DAO) is used as a component of, or as the entire, fresh feed component, the unconverted oil can have a distillation end point of at least about 700° C.

The term "T1" or "T99" means the temperature at which 1 liquid volume percent or 99 liquid volume percent, as the case may be, respectively, of the sample boils using ASTM D86, ASTM D2892 or ASTM D7169, as the case may be.

The terms "wt. %", "vol. %", or "mol. %" refers to a weight, volume, or molar percentage of a component, respectively, based on the total weight, the total volume of material, or total moles, that includes the component. In a non-limiting example, 10 grams of component in 100 grams of the material is 10 wt. % of component.

In general, the process of the present disclosure may be used to reduce the concentration of polycyclic aromatic hydrocarbon contaminants from a hydrocarbon stream using a quinolinium-based ionic liquid.

Hydrocarbon Oil

A variety of hydrocarbon feeds may be treated herein. In general, they contain at least 10% by volume, generally at least 20% by volume, at least 50% by volume, and often at least 80% by volume of compounds boiling above 340° C.

The hydrocarbon feed stream may be, for example an unconverted oil (UCO) obtained from a hydrocracking unit. A typical hydrocracking feedstock is a vacuum gas oil (VGO) stream. VGO can include hydrocarbons having a boiling temperature in a range of about 343° C. to 565° C. Heavy feedstreams such as demetallized oil (DMO) or deasphalted oil (DAO), alone or blended with VGO can be processed in a hydrocracking unit. Undiluted DMO or DAO can also be processed, but typically under more severe conditions, since the DMO or DAO stream contains a higher concentration of impurities (e.g., nitrogen, sulfur and HPNA precursors) than the VGO stream. DAO denotes an oil from which a fraction of asphaltenes has been removed and can include hydrocarbons having a boiling temperature in a range of about 300° C. to about 900° C. (e.g., about 350° C. to 850° C., or about 400° C. to about 800° C.)

The ionic liquid can remove or more polycyclic aromatic hydrocarbon contaminants in the hydrocarbon feed stream. The hydrocarbon feed stream will generally comprise a plurality of heavy polynuclear aromatic (HPNA) contaminants of different types and in various amounts. The presence of HPNA contaminants in the hydrocarbon stream can be detrimental to further processing. Thus, at least a portion of at least one type of HPNA compound may be removed from the hydrocarbon feed. The same or different amounts of each type of HPNA compound can be removed, and some types of HPNA compounds may not be removed. The HPNA content of the hydrocarbon feed can be reduced by at least 10% by weight, or at least 20% by weight, or at least 30% by weight, or at least 40% by weight, or at least 50%, or at least 60% by weight, or at least 70%, or at least 80 wt. %, or at least 90 wt. %, or at least 95 wt. %.

The total HPNA content of the hydrocarbon feed stream can be in a range of about 50 ppm to 5 wt. % or more. The HPNA content may be determined using high-performance liquid chromatography (HPLC) coupled with fluorescence analysis or by high resolution mass spectrometry or by the combination of any of these techniques. Representative HPNA compounds most easily identifiable and quantifiable by such analytical techniques include dibenzo[ghi]perylene, coronene and ovalene.

The hydrocarbon feed stream may also comprise a plurality of asphaltene contaminants of different types in various amounts. Asphaltenes can aggregate and form deposits in diverse locations during petroleum production operations. The asphaltenes content of the hydrocarbon stream to be treated in the present processes may be less than 3000 ppm by weight, or less than 1000 ppm by weight, or less than 300 ppm by weight. In some aspects, the asphaltene content of the hydrocarbon feed stream can be reduced by at least 10% by weight, or at least 20% by weight, or at least 25% by weight, or at least 30% by weight, or at least 40% by weight, or at least 50% by weight.

Ionic Liquid

Ionic liquids suitable for use herein are hydrocarbon-immiscible quinolinium ionic liquids. As used herein, the term "hydrocarbon-immiscible quinolinium ionic liquid" means that the quinolinium-based ionic liquid is capable of forming a separate phase hydrocarbon feed under operating conditions of the process. Quinolinium ionic liquids that miscible with the hydrocarbon feed at the process conditions will be completely soluble with the hydrocarbon feed; therefore, no phase separation will be feasible. Thus, hydrocarbon-immiscible quinolinium ionic liquids may be insoluble with or partially soluble with the hydrocarbon feed under the operating conditions. A quinolinium ionic liquid capable of forming a separate phase from the hydrocarbon feed under the operating conditions is considered to be hydrocarbon-immiscible. Quinolinium ionic liquids according to the present disclosure may be insoluble, partially soluble, or completely soluble (miscible) with water.

Consistent with common terms of the art, the quinolinium ionic liquid introduced to the contaminant removal zone may be referred to as a "lean" quinolinium ionic liquid, which generally means a hydrocarbon-immiscible quinolinium ionic liquid that is not saturated with one or more extracted contaminants. Lean quinolinium ionic liquid may include one or both of fresh and regenerated quinolinium ionic liquid and is suitable for accepting or extracting contaminants from the hydrocarbon feed. Likewise, the quinolinium ionic liquid may be referred to as "rich", which generally means a hydrocarbon-immiscible quinolinium ionic liquid effluent produced by a contaminant removal step or process or otherwise including a greater amount of extracted contaminants than the amount of extracted contaminants included in the lean quinolinium ionic liquid. A rich quinolinium ionic liquid may require regeneration or dilution (e.g., with fresh quinolinium ionic liquid) before recycling the rich quinolinium ionic liquid to the same or another contaminant removal step of the process.

Generally, ionic liquids are non-aqueous, organic salts composed of ions where the positive ion is charge balanced with a negative ion. These materials have low melting points, often below 100° C. The cationic charge of the salt is localized over heteroatoms, such as nitrogen, phosphorus and sulfur, and the anions may be any inorganic, organic, or organometallic species.

In some aspects, the quinolinium ionic liquid may be of the general formula:

where R may be hydrogen, an alkyl group having from 1 to 12 carbon atoms (e.g., 1 to 4 carbon atoms), an amine, an ether, or a silyl group; and anion $A^-$ may be selected from the group consisting of chloride, bromide, iodide, nitrate, sulfate, tetrafluoroborate, hexafluorophosphate, acetates, haloacetates (e.g., trifluoroacetate, chloroacetate), alkylsulfonates (e.g., methanesulfonate), perfluoroalkanesulfonates (e.g., trifluoromethanesulfonate), bis(perfluoroalkanesulfonyl)imides such as bis(trifluoromethanesulfonyl)imide, and arene sulfonates (e.g., p-toluenesulfonate). In some aspects, the anion $A^-$ is bis(trifluoromethanesulfonyl)imide.

In some aspects, the hydrocarbon-immiscible quinolinium ionic liquid comprises at least one of N-benzylquinolinium bis(trifluoromethanesulfonyl)imide, N-benzyl-6-methylquinolinium bis(trifluoromethanesulfonyl)imide, N-benzyl-6-isopropylquinolinium bis(trifluoromethanesulfonyl)imide, N-benzyl-6-isopropylquinolinium bis(trifluoromethanesulfonyl)imide, and N-benzyl-6-methoxyquinolinium bis(trifluoromethanesulfonyl)imide.

Extraction Process

Solvent extraction, also referred to as liquid-liquid extraction or partitioning, is a method of separating compounds based on their relative solubilities, for example in at least two immiscible liquids. Liquid-liquid extraction is a basic chemical technique and is readily scalable. Thus, it may be applied on a smaller scale in laboratories using, for example, a separatory funnel, as well as on an industrial scale using, for example, large separation towers or columns discussed in more detail below.

The process for removing polycyclic aromatic hydrocarbon contaminants from a hydrocarbon feed stream comprises a contacting step and a separating step. In the contacting step, a hydrocarbon stream comprising a contaminant and a hydrocarbon-immiscible quinolinium ionic liquid are mixed or otherwise brought into contact with each other. The contacting step may facilitate transfer or extraction of the one or more contaminants from the hydrocarbon feed stream to the quinolinium ionic liquid. Although a quinolinium ionic liquid that is partially soluble in the hydrocarbon may facilitate transfer of the contaminant from the hydrocarbon to the quinolinium ionic liquid, partial solubility is not required. Insoluble hydrocarbon/quinolinium ionic liquid mixtures may have sufficient interfacial surface area between the hydrocarbon and the quinolinium ionic liquid to be useful. In the separation step, the mixture of hydrocarbon and quinolinium ionic liquid settles or forms two phases, a hydrocarbon phase and a quinolinium ionic liquid phase, which are separated to produce a hydrocarbon effluent and a hydrocarbon-immiscible quinolinium ionic liquid effluent.

The process may be conducted in various equipment which is well known in the art and is suitable for batch or continuous operation. For example, in a small-scale form of the process, the hydrocarbon and the hydrocarbon-immiscible quinolinium ionic liquid may be mixed in a beaker, flask, or other vessel, e.g., by stirring, shaking, use of a mixer, or a magnetic stirrer. The mixing or agitation is stopped, and the mixture forms a hydrocarbon phase and a quinolinium ionic liquid phase which can be separated, for example, by decanting, centrifugation or other means to produce a hydrocarbon effluent having a lower contaminant content relative to the incoming hydrocarbon. The process also produces a hydrocarbon-immiscible quinolinium ionic liquid effluent comprising the one or more contaminants.

In large-scale commercial operations, the process may occur in any suitable apparatus known in the art capable of performing liquid-liquid extraction. Suitable extractors include centrifugal contactors and contacting columns such as tray columns, spray columns, packed towers, rotating disc contactors and pulse columns.

The process, including contacting the hydrocarbon feed stream containing the contaminant with the lean hydrocarbon-immiscible liquid stream, may take place in a co-current mode, in which the immiscible liquids (e.g., the hydrocarbon and the hydrocarbon-immiscible quinolinium ionic liquid streams) flow in the same direction. Alternatively, the process may take place in a counter-current mode, where the immiscible liquids flow in opposite directions.

The contacting and separating steps can be repeated, for example, when the contaminant content of the hydrocarbon effluent is to be reduced further to obtain a desired contaminant level in the ultimate hydrocarbon product stream from the process. Each set, group, or pair of contacting and separating steps may be referred to as a contaminant removal step. Thus, the present process encompasses single and multiple contaminant removal steps. A contaminant removal zone may be used to perform a contaminant removal step. As used herein, the term "zone" can refer to one or more equipment items and/or one or more sub-zones. Equipment items may include, for example, one or more vessels, heaters, separators, exchangers, conduits, pumps, compressors, and controllers. The contaminant removal process or step may be conducted in a similar manner and with similar equipment as is used to conduct other liquid-liquid wash and extraction operations. Suitable equipment includes, for example, columns with trays, packing, rotating discs or plates, and static mixers. Pulse columns and mixing/settling tanks may also be used.

Figure 1:
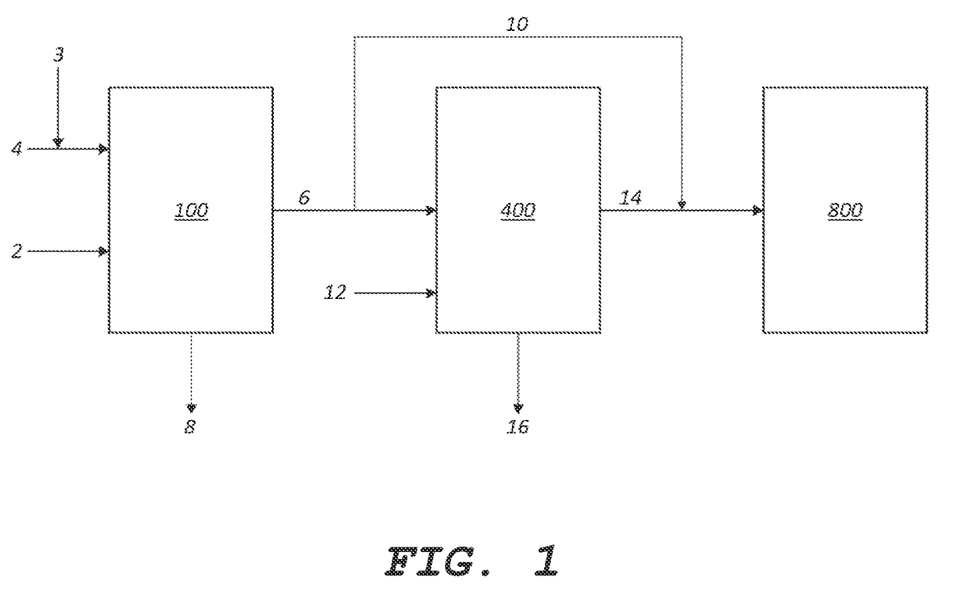
FIG. 1 is a simplified flow scheme illustrating various aspects of the present disclosure.

FIG. 1 is a flow scheme illustrating various aspects of the presently disclosed technology and some of the optional and/or alternate steps and apparatus encompassed by the technology. Hydrocarbon feed stream 2 and hydrocarbon-immiscible quinolinium ionic liquid stream 4 are introduced to and contacted and separated in contaminant removal zone 100 resulting in hydrocarbon-immiscible quinolinium ionic liquid effluent stream 8 and hydrocarbon effluent stream 6 as described above.

The ionic liquid stream 4 may be comprised of fresh quinolinium ionic liquid stream 3 and/or one or more quinolinium ionic liquid streams which are recycled. In an embodiment, a portion or all of hydrocarbon effluent stream 6 is passed via conduit 10 to a hydrocarbon conversion zone 800. Hydrocarbon conversion zone 800 may, for example, comprise at least one of a fluid catalytic cracking and a hydrocracking process, which are well known in the art.

The contacting step can take place at a temperature in a range of about 15° C. to the decomposition temperature of the ionic liquid, or 15° C. to 150° C., or 15° C. to 120° C., or 15° C. to 100° C., or 15° C. to 80° C.

The contacting step typically takes place at atmospheric pressure, although higher or lower pressures could be used, if desired. The pressure can be in a range of about 100 kPa(g) to 3 MPa(g).

The contacting time is sufficient to obtain good contact between the ionic liquid and the hydrocarbon feed. The contacting time may be in a range of from 1 minute to 2 hours (e.g., 1 minute to 1 hour, or 5 minutes to 30 minutes). The settling time may be in a range of from 1 minute to 8 hours (e.g., 1 minute to 2 hours, or 1 minute to 1 hour, or 1 minute to 30 minutes, or 1 minute to 10 minutes).

The weight ratio of hydrocarbon feed to lean hydrocarbon-immiscible ionic liquid introduced to the contacting step may be in a range from 1:10,000 to 10,000:1 (e.g., 1:1000 to 1000:1, or 1:100 to 100:1, or 1:20 to 20:1, or 1:10 to 10:1). In some aspects, the weight of hydrocarbon feed is greater than the weight of ionic liquid introduced to the contacting step.

An optional hydrocarbon washing step may be used, for example, to recover ionic liquid that is entrained or otherwise remains in the hydrocarbon effluent stream by using water to wash or extract the ionic liquid from the hydrocarbon effluent. In this aspect, a portion or all of hydrocarbon effluent stream 6 (as feed) and a water stream 12 (as solvent) are introduced to hydrocarbon washing zone 400. The hydrocarbon effluent and water streams introduced to hydrocarbon washing zone 400 are mixed and separated to produce a washed hydrocarbon stream 14 and a spent water stream 16, which comprises the ionic liquid. The hydrocarbon washing step may be conducted in a similar manner and with similar equipment as used to conduct other liquid-liquid wash and extraction operations as discussed above. Various hydrocarbon washing step equipment and conditions such as temperature, pressure, times, and solvent to feed ratio may be the same as or different from the contaminant removal zone equipment and conditions. In general, the hydrocarbon washing step conditions will fall within the same ranges as given for the contaminant removal step conditions. A portion or all of the washed hydrocarbon stream 14 may be passed to hydrocarbon conversion zone 800.

Alternatively, hydrocarbon-immiscible quinolinium ionic liquid that is entrained or otherwise remains in the hydrocarbon effluent stream may be removed from the hydrocarbon by contacting the effluent stream with a retaining material for retaining at least a portion of the entrained ionic liquid. The retaining material may comprise an adsorbent material, although other materials may be used. Oxides and oxide materials such as silica, alumina, and silica-alumina could be used as adsorbents in granular, fiber, pellet, or other form. Other adsorbents may include ion exchange resins, activated carbon, clays, and molecular sieves. In some instances, it may be desirable to retain the hydrocarbon-immiscible ionic liquid so as to minimize the amount of hydrocarbon-immiscible ionic liquid that is passed to downstream equipment to avoid fouling or damaging the equipment. The hydrocarbon-immiscible ionic liquid may be burned off of the spent or saturated adsorbent under calcination conditions which would regenerate spent adsorbent allowing the adsorbent to be reused. Alternatively, the spent adsorbent may be disposed of as a waste product and replaced with fresh adsorbent. In some instances, it may be desirable to recover some or all of the hydrocarbon-immiscible ionic liquid from the retaining material. Accordingly, a solvent or a desorbent may be used to remove the hydrocarbon-immiscible ionic liquid from the retaining material. For example, an ionic liquid precursor, a second and different ionic liquid, inert liquid, benzene, and toluene may be used as a solvent. The desorbent could be something in which the hydrocarbon-immiscible ionic liquid is soluble and operate via a solubility mechanism, such as a chlorosilane or an organic halide such as methylene chloride or chlorobenzene. In some cases, recovered hydrocarbon-immiscible ionic liquid may not be in active form when recovered. The recovered hydrocarbon-immiscible liquid can be reactivated by addition of a reactivation agent.

Figure 2A:
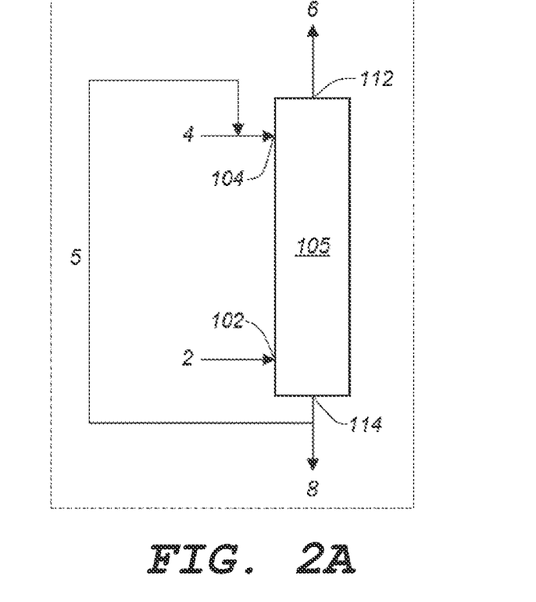
FIGS. 2A and 2B are simplified flow schemes illustrating different aspects of an extraction zone of the present disclosure.

FIG. 2A illustrates an aspect of the present disclosure which may be practiced in contaminant removal or extraction zone 100 that comprises a multi-stage, counter-current extraction column 105 wherein hydrocarbon and hydrocarbon-immiscible ionic liquid are contacted and separated. The hydrocarbon feed stream 2 enters extraction column 105 through hydrocarbon feed inlet 102, and lean hydrocarbon-immiscible quinolinium ionic liquid stream 4 enters extraction column 105 through ionic liquid inlet 104. In the Figures, reference numerals of the streams and the lines or conduits in which they flow are the same. Hydrocarbon feed inlet 102 is located below ionic liquid inlet 104. The hydrocarbon effluent passes through hydrocarbon effluent outlet 112 in an upper portion of extraction column 105 to hydrocarbon effluent conduit 6. The hydrocarbon-immiscible ionic liquid effluent including the contaminants removed from the hydrocarbon feed passes through ionic liquid effluent outlet 114 in a lower portion of extraction column 105 to ionic liquid effluent conduit 8.

Optionally, a portion or all of the hydrocarbon-immiscible quinolinium ionic liquid effluent stream is recycled back to the top of extraction column 105 via conduit 5. In some aspects, when the contaminant concentration increases to a pre-determined level, a portion of the ionic liquid effluent stream comprising the contaminant is drained out of the system via conduit 8. In some aspects, a slip stream of the ionic liquid effluent stream comprising the contaminant is continuously purged from the system via conduit 8 and a lean hydrocarbon-immiscible quinolinium ionic liquid stream 4 is continuously injected into the system to maintain a certain contaminant concentration in the ionic liquid circulation flow.

Figure 2B:
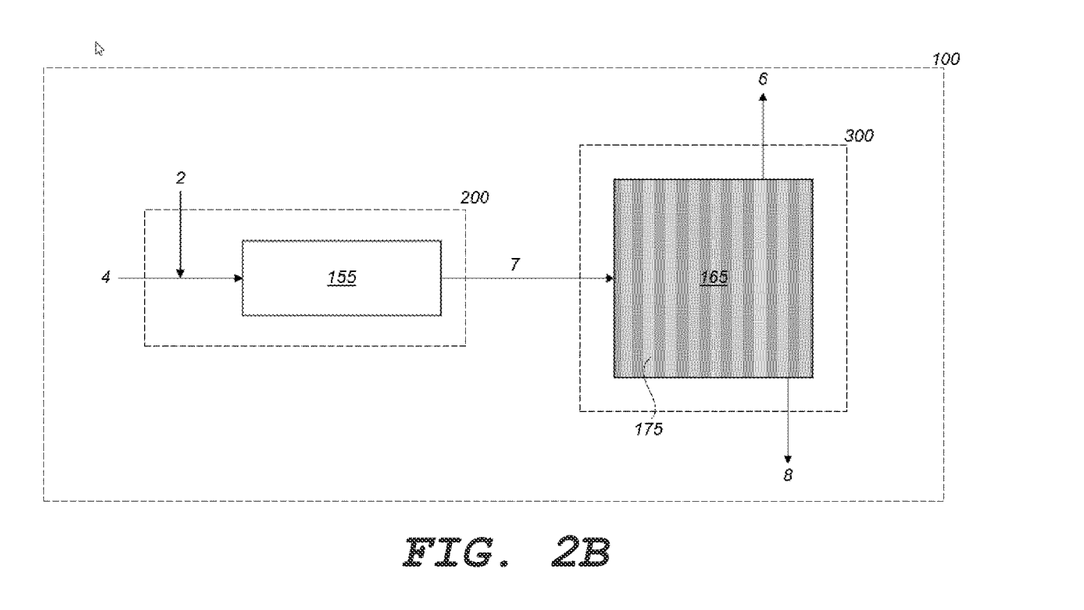

FIG. 2B illustrates another aspect of contaminant removal zone 100 that comprises a contacting zone 200 and a separation zone 300. In this aspect, lean hydrocarbon-immiscible quinolinium ionic liquid stream 4 and hydrocarbon feed stream 2 are introduced into the contacting zone 200 and mixed by introducing hydrocarbon feed stream 2 into the flowing lean hydrocarbon-immiscible quinolinium ionic liquid stream 4 and passing the combined streams through static in-line mixer 155. Static in-line mixers are well known in the art and may include a conduit with fixed internals such as baffles, fins, and channels that mix the fluid as it flows through the conduit. In other aspects, not illustrated, lean hydrocarbon-immiscible quinolinium ionic liquid stream 4 may be introduced into hydrocarbon feed stream 2, or the lean hydrocarbon-immiscible ionic liquid stream 4 and hydrocarbon feed stream 2 are separately introduced into the static in-line mixer 155. In other aspects, the streams may be mixed by any method known in the art, including stirred tank and blending operations. The mixture comprising hydrocarbon and hydrocarbon-immiscible ionic liquid is transferred to separation zone 300 via transfer conduit 7. Separation zone 300 comprises separation vessel 165 wherein two phases are allowed to separate into a rich hydrocarbon-immiscible ionic liquid phase which is withdrawn from a lower portion of separation vessel 165 via ionic liquid effluent conduit 8 and a hydrocarbon phase which is withdrawn from an upper portion of separation vessel 165 via hydrocarbon effluent conduit 6. Separation vessel 165 may comprise a boot, not illustrated, from which contaminant rich ionic liquid is withdrawn via conduit 8.

Separation vessel 165 may contain a solid media 175 and/or other coalescing devices which facilitate the phase separation. In other aspects, the separation zone 300 may comprise multiple vessels which may be arranged in series, parallel, or a combination thereof. The separation vessels may be of any shape and configuration to facilitate the separation, collection, and removal of the two phases. In a further aspect, contaminant removal zone may include a single vessel wherein lean hydrocarbon-immiscible quinolinium ionic liquid stream 4 and hydrocarbon feed stream 2 are mixed, then remain in the vessel to settle into the hydrocarbon effluent and rich ionic liquid phases.

In one aspect, the process can comprise two or more contaminant removal steps. For example, the hydrocarbon effluent from one contaminant removal step may be passed directly as the hydrocarbon feed to a second contaminant removal step. In another aspect, the hydrocarbon effluent from one contaminant removal step may be treated or processed before being introduced as the hydrocarbon feed to the second contaminant removal step. There is no requirement that each contaminant removal zone comprises the same type of equipment. Different equipment and conditions may be used in different contaminant removal zones.

The contaminant removal step may be conducted under contaminant removal conditions including temperatures and pressures sufficient to keep the hydrocarbon-immiscible ionic liquid and hydrocarbon feeds and effluents as liquids. For example, the contaminant removal step temperature may be in a range of from 15° C. to less than the decomposition temperature of the quinolinium ionic liquid, and the pressure may range in a range of from about 100 kPa(g) to 700 kPa(g). When the hydrocarbon-immiscible quinolinium ionic liquid comprises more than one quinolinium ionic liquid component, the decomposition temperature of the quinolinium ionic liquid is the lowest temperature at which any of the quinolinium ionic liquid components decompose. The contaminant removal step may be conducted at a uniform temperature and pressure or the contacting and separating steps of the contaminant removal step may be operated at different temperatures and/or pressures.

Figure 3:
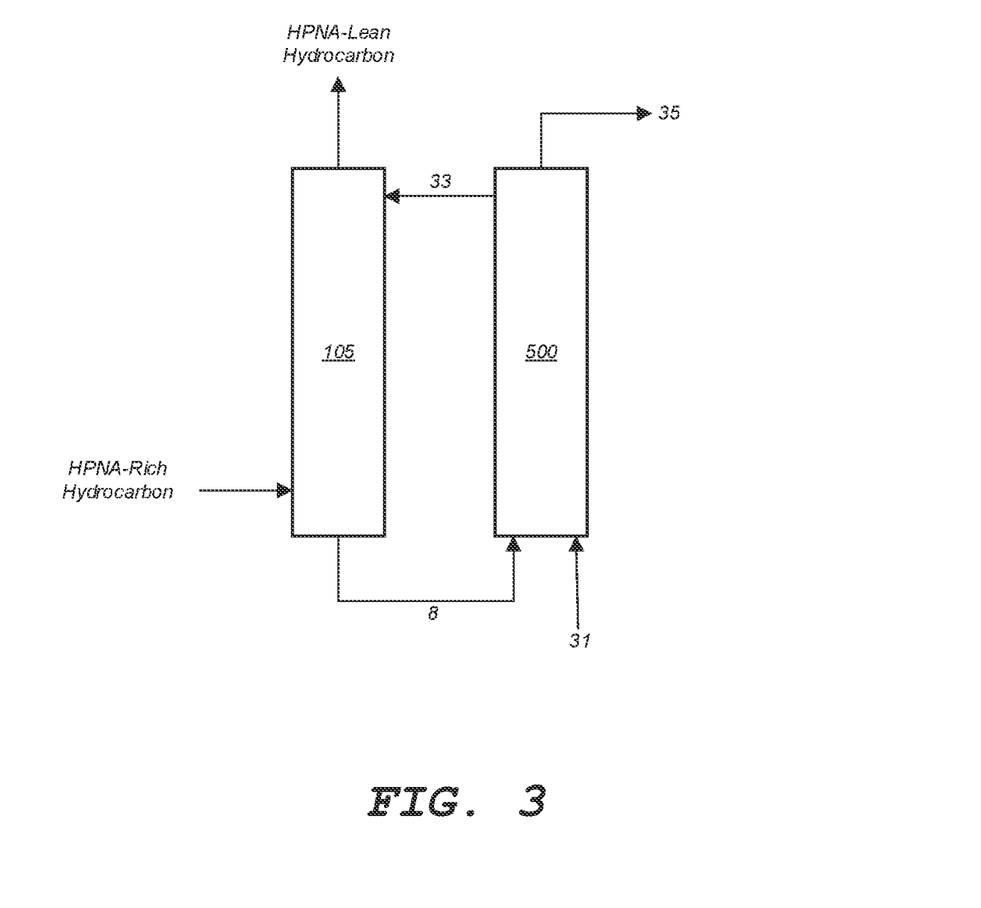
FIG. 3 is a simplified process flow diagram illustrating one aspect of a hydrocarbon-immiscible ionic liquid regeneration process.

An optional regeneration step may be used, for example, to regenerate the ionic liquid by removing the contaminant from the ionic liquid (i.e., reducing the HPNA content of the rich hydrocarbon-immiscible ionic liquid effluent). In one aspect illustrated in FIG. 3, a portion or all of the hydrocarbon-immiscible quinolinium ionic liquid effluent stream comprising the HPNA contaminant is introduced to hydrocracking zone 500 via conduit 8. The hydrocarbon-immiscible quinolinium ionic liquid effluent stream comprising the HPNA contaminant is contacted with hydrogen 31 under hydrocracking conditions with or without a hydrocracking catalyst. Any conventional hydrocracking reactor can be used. When regeneration is conducted without a catalyst, a bubble column can be used where trays are used to separate the reactor into several vertical compartments and hydrogen 31 is provided to a lower portion of the reactor, allowing a plug-flow scheme for both hydrogen 31 and the hydrocarbon-immiscible quinolinium ionic liquid effluent stream 8 comprising the HPNA compound. In hydrocracking zone 500, a portion or all of HPNA compounds having less than 5 rings are "cracked" to form lower molecular weight hydrocarbons. The process typically also generates light side products including hydrogen, carbon oxides, light ends, and water. The light ends represent a mix of low weight hydrocarbon compounds, such as methane or ethane. These light gas products are removed in an off-gas stream in an upper portion of regeneration zone 500 via conduit 35. A portion or all of the regenerated hydrocarbon-immiscible quinolinium ionic liquid is recycled via conduit 33 back to multi-stage, counter-current extraction column 105 after cooling down to the extraction temperatures.

Suitable hydrocracking catalysts include amorphous silica-alumina bases or low-level zeolite bases combined with one or more Group VIII or Group VIB metal hydrogenating components, or a crystalline zeolite cracking base upon which is deposited a Group VIII metal hydrogenating component. Hydrocracking conditions may include a temperature of 149° C. to 468° C. (300° F. to 875° F.), a pressure of 2.1 to 20.7 MPa (300 to 3000 psig), a liquid hourly space velocity (LHSV) of 0.05 to less than 2.5 h$^{-1}$, and a hydrogen rate of 51 to 2527 Nm$^3$/m$^3$ (300 to 15,000 scf/bbl).

Figure 4:
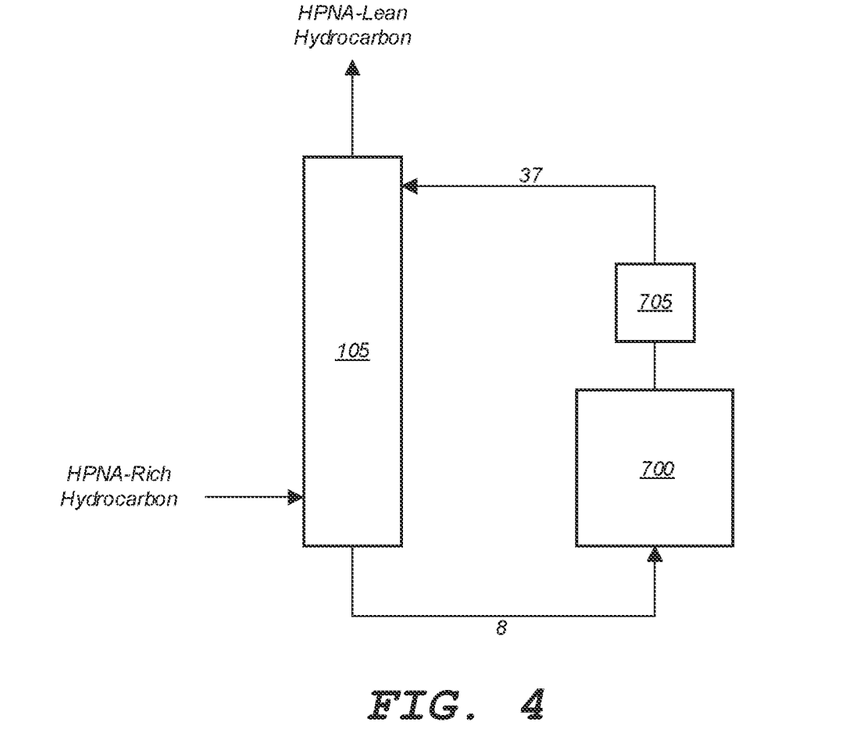
FIG. 4 is a simplified process flow diagram illustrating another aspect of a hydrocarbon-immiscible ionic liquid regeneration process.

Regeneration of the hydrocarbon-immiscible ionic liquid effluent containing the HPNA compound can comprise crystallizing the HPNA compound from the rich hydrocarbon-immiscible quinolinium ionic liquid effluent. In one aspect illustrated in FIG. 4, a portion or all of the hydrocarbon-immiscible quinolinium ionic liquid effluent stream comprising the HPNA compound is introduced to crystallization zone 700 via conduit 8. The crystallization zone 700 can include one or more crystallizers. One or more crystallizers are used to facilitate the crystallization of the HPNA compound at lower temperatures. The crystallized HPNA compound is separated from the solvent in a separator zone 705. The separator zone 705 can include one or more of filters, centrifuges, and dryers, as is known in the art. A portion or all of the regenerated hydrocarbon-immiscible quinolinium ionic liquid is recycled via conduit 37 back to multi-stage, counter-current extraction column 105.

Regeneration of the hydrocarbon-immiscible liquid effluent can comprise contacting the hydrocarbon-immiscible quinolinium liquid effluent rich in HPNA compounds with a polar organic solvent in a separation unit for a time sufficient to form a solution of the HPNA compound in the polar organic solvent. A portion or all of the HPNA compound will be transferred to the organic phase allowing for the HPNA compound to be removed from the hydrocarbon-immiscible quinolinium ionic liquid. Regenerated hydrocarbon-immiscible ionic liquid can be recovered from the separation unit and recycled to the contaminant removal zone. The polar organic solvent containing the HPNA compound can be sent to a solvent recovery unit where a solvent stream can be recovered and recycled to the separation unit.

Recovered HPNA compounds can be further processed in a delayed coker to produce high quality coke, and/or gasified to produce hydrogen, steam and electricity, and/or can be sent to the fuel oil pool as blending components, and/or can be sent to an FCC unit to form a small portion of the FCC feedstream and eventually be deposited as coke on the catalyst, which coke will be burned to produce heat in the catalyst regeneration step, and/or can be sent to the asphalt pool.

EXAMPLES

The following illustrative examples are intended to be non-limiting.

Figure 5:
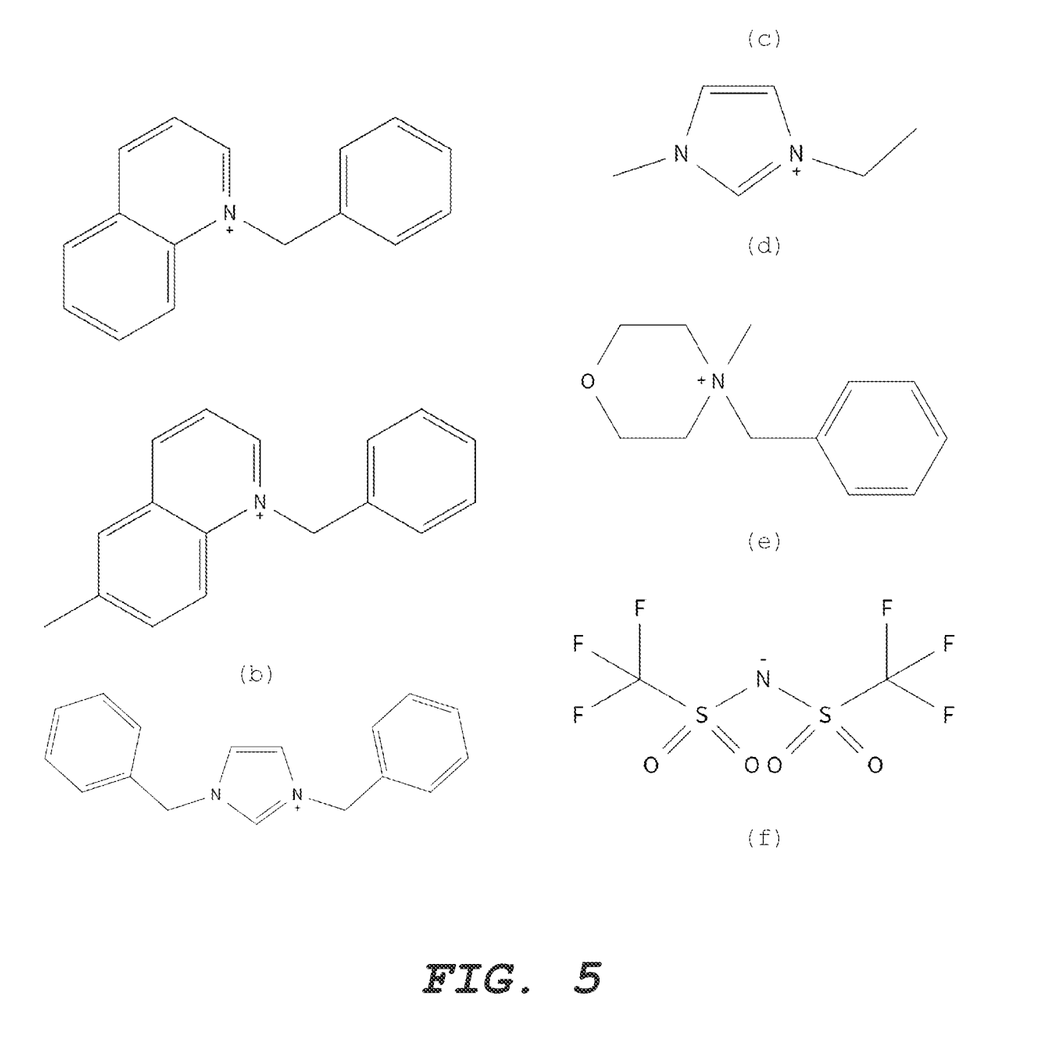
FIG. 5 shows structures of the ionic liquid cations (a) N-benzylquinolinium [BzQuin], (b) N-benzyl-6-methylquinolinium [Bz6MQuin], (c) 1,3-dibenzylimidazolium [DBzIm], (d) 1-ethyl-3-methylimidazolium [EMIm], (e) N-benzyl-N-methylmorpholinium [BzMMorp], and (f) bis(trifluoromethylsulfonyl)imide [$Tf_2N$] anion used in the Examples.

FIG. 5 shows structures of the ionic liquid cations (a) N-benzylquinolinium [BzQuin], (b) N-benzyl-6-methylquinolinium [Bz6MQuin], (c) 1,3-dibenzylimidazolium [DBzIm], (d) 1-ethyl-3-methylimidazolium [EMIm], (e) N-benzyl-N-methylmorpholinium [BzMMorp], and (f) bis(trifluoromethanesulfonyl)imide [Tf$_2$N] anion used in the Examples.

Example 1

Preparation of N-Benzylquinolinium Bis(trifluoromethanesulfonyl)imide [BzQuin] [Tf$_2$N] Ionic Liquid A three-neck round bottom flask was charged with quinoline (50 g, 0.39 mol) and methanol (250 mL). Benzyl chloride (73.5 g, 0.58 mol) was then added. The mixture was stirred at room temperature for about 5 days and then heated at reflux for 48 hours. After cooling, the mixture was transferred to a rotatory evaporator and concentrated under reduced pressure to provide a viscous oil. The oil was washed with diethyl ether (100 mL) and tetrahydrofuran (50 mL). The washed oil was then concentrated under reduced pressure on a rotatory evaporator at 75° C. for 1 hour to provide 1-benzylquinolinium chloride (92 g, 93% yield).

1-Benzylquinolinium chloride (50 g, 0.195 mol) was dissolved in distilled water (250 mL). Lithium bis(trifluoromethanesulfonyl)imide (56 g, 0.195 mol) was then added. The mixture was stirred at room temperature overnight and then at reflux for about 1 hour. After cooling, the mixture was transferred to a separatory funnel and allowed to settle. The ionic liquid layer was collected, transferred to a rotary evaporator and concentrated under reduced pressure at 85° C. for about 4 hours. The product, 1-benzylquinolinium bis(trifluoromethanesulfonyl)imide, was obtained as a viscous colorless oil (89 g, 91% yield).

Example 2

Preparation of N-Benzyl-6-methylquinolinium Bis((trifluoromethanesulfonyl)imide [Bz6MQuin] [Tf$_2$N] Ionic Liquid A three-neck round bottom flask was charged with 6-methylquinoline (50 g, 0.35 mol) and methanol (250 mL). Benzyl chloride (67 g, 0.53 mol) was then added. The mixture was stirred at room temperature for about 6 days and then at reflux for 24 hours. After cooling, the mixture was transferred to a rotary evaporator and concentrated under reduced pressure to provide a viscous oil. The oil was washed with diethyl ether (1×100 mL and 1×50 mL). The washed oil was concentrated under reduced pressure on a rotatory evaporator at 75° C. for 1 hour to provide 1-benzyl-6-methylquinolinium chloride (87 g, 93% yield).

1-Benzyl-6-methylquinolinium chloride (50 g, 0.185 mol) was dissolved in distilled water (250 mL). Lithium bis(trifluoromethanesulfonyl)imide (51.8 g, 0.185 mol) was then added. The mixture was stirred at room temperature overnight and then at reflux for about 1 hour. After cooling, the mixture was transferred to a separatory funnel and allowed to settle. The ionic liquid layer was collected, transferred to a rotatory evaporator and concentrated under reduced pressure at 85° C. for about 4 hours. The product, N-benzyl-6-methylquinolinium bis(trifluormethanesulfony)imide, was obtained as a viscous colorless oil (86 g, 91% yield).

Examples 3-4

Liquid-Liquid Extraction with [BzQuin] [Tf$_2$N]

1-Benzyl quinolinium bis(trifluoromethanesulfonyl)imide ionic liquid (3 g) was mixed with a recycle oil (12 g) from a two-stage recycle hydrocracking unit. The resulting biphasic mixture was vigorously stirred at 20° C. or at 93° C. for 2 hours using a magnetic stirring bar. The mixture was then centrifuged at 4000 rpm for 20 minutes at 30° C. The treated oil phase was collected and analyzed for HPNA compounds by high-performance liquid chromatography (HPLC) methods. The results are summarized in Table 1.

Examples 5-6

Liquid-Liquid Extraction with [Bz6MQuin] [Tf$_2$N]

The process of Examples 3-4 was repeated using 1-benzyl-6-methylquinolinium bis(trifluoromethanesulfonyl)imide, [Bz6MQuin] [Tf$_2$N], as the ionic liquid. The results are summarized in Table 1.

Example 7 (Comparative)

Liquid-Liquid Extraction with [DBzIm] [Tf$_2$N]

The process of Example 1 was repeated using 1,3-dibenzylimidazolium bis(trifluoromethanesulfonyl)imide, [DBzIm] [Tf$_2$N], as the ionic liquid. The results are summarized in Table 1.

Example 8 (Comparative)

Liquid-Liquid Extraction with [EMIm] [Tf$_2$N]

The process of Examples 3-4 was repeated using 1-ethyl-3-methylimidazolium bis(trifluoromethanesulfonyl)imide, [EMIm] [Tf$_2$N], as the ionic liquid. The results are summarized in Table 1.

Examples 9-10 (Comparative)

Liquid-Liquid Extraction with [BzMMorp] [Tf$_2$N]

The process of Examples 3-4 was repeated using N-benzyl-N-methylmorpholinium bis(trifluormethanesulfonyl)imide, [BzMMorp] [Tf$_2$N], as the ionic liquid. The results are summarized in Table 1.

TABLE 1

HPNA Distribution in Untreated Recycle Oil and Treated Recycle Oils of Examples 3-10

| | Untreated Recycle Oil | Ex. 3 | Ex. 4 | Ex. 5 | Ex. 6 | Ex. 7 | Ex. 8 | Ex. 9 | Ex. 10 |
|---|---|---|---|---|---|---|---|---|---|
| Ionic Liquid Treatment | — | [BzQuin] [Tf$_2$N] | [BzQuin] [Tf$_2$N] | [Bz6MQuin] [Tf$_2$N] | [Bz6MQuin] [Tf$_2$N] | [DBZIm] [Tf$_2$N] | [EMIm] [Tf$_2$N] | [BzMMorp] [Tf$_2$N] | [BzMMorp] [Tf$_2$N] |
| Treatment Temperature [° C.] | — | 20 | 93 | 20 | 93 | 93 | 93 | 20 | 93 |
| HPNA Content [ppm] | | | | | | | | | |
| Benzo [ghi] perylene | 309 | 42 | 74 | 16 | 32 | 264 | 198 | 243 | 240 |
| Methyl Benzo [ghi] perylene | 194 | 28 | 47 | 11 | 21 | 159 | 188 | 149 | 146 |
| Coronene | 206 | 24 | 48 | 10 | 19 | 187 | 207 | 180 | 170 |
| Methyl Coronene | 12 | 0 | 0 | 0 | 0 | 0 | 0 | 0 | 0 |
| Ovalene | 0 | 0 | 0 | 0 | 0 | 0 | 0 | 0 | 0 |

The results presented in Table 1 show that N-benzylquinolinium ionic liquids of Examples 3-6 are effective in removing heavy polycyclic aromatic hydrocarbon contaminants from hydrocarbon streams.

The invention claimed is:
1. A process for removing a contaminant comprising at least one polynuclear aromatic compound from a hydrocarbon stream, the process comprising
(a) contacting the hydrocarbon stream comprising the contaminant with a hydrocarbon-immiscible quinolinium ionic liquid under contacting conditions to produce a mixture comprising the hydrocarbon and the hydrocarbon-immiscible quinolinium ionic liquid, wherein the hydrocarbon-immiscible quinolinium ionic liquid comprises at least a portion of the removed contaminant; and
(b) separating the mixture to produce a hydrocarbon effluent having a reduced level of the contaminant and a hydrocarbon-immiscible quinolinium ionic liquid effluent comprising the hydrocarbon-immiscible quinolinium ionic liquid and at least the portion of the removed contaminant;
wherein the hydrocarbon-immiscible quinolinium ionic liquid is of formula:

where R is selected from hydrogen, an alkyl group having from 1 to 12 carbon atoms, an amine, an ether, or a silyl group; and anion A⁻is selected from chloride, bromide, iodide, nitrate, sulfate, tetrafluoroborate, hexafluorophosphate, acetates, haloacetates, alkanesulfonates, perfluoroalkanesulfonates, bis(perfluoroalkanesulfonyl)imides, and arene sulfonates.

2. The process of claim 1, wherein R is selected from hydrogen and an alkyl group having from 1 to 4 carbon atoms.

3. The process of claim 1, wherein the anion A⁻is bis(trifluoromethanesulfonyl)imide.

4. The process of claim 1, wherein the hydrocarbon stream comprises at least 50% by volume of compounds boiling above 340° C.

5. The process of claim 1, wherein the hydrocarbon stream is an unconverted oil from a hydrocracking unit.

6. The process of claim 1, wherein the contacting conditions include a temperature in a range of from 15° C. to 150° C. and a pressure in a range of from 100 kPa to 3 MPa.

7. The process of claim 1, wherein a weight ratio of the hydrocarbon stream to the hydrocarbon-immiscible quinolinium ionic liquid is in a range of from 1:1000 to 1000:1.

8. The process of claim 1, further comprising passing at least a portion of the hydrocarbon effluent to a hydrocarbon conversion process.

9. The process of claim 1, wherein the contaminant further comprises asphaltenes.

10. The process of claim 9, wherein the asphaltenes content is less 3000 ppm by weight.

11. The process of claim 1, further comprising:
recycling at least a portion of the hydrocarbon-immiscible quinolinium ionic liquid effluent back to the contacting step.

12. The process of claim 1, further comprising:
regenerating at least a portion of the hydrocarbon-immiscible quinolinium ionic liquid effluent comprising the polynuclear aromatic compound; and
recycling the regenerated hydrocarbon-immiscible quinolinium ionic liquid to the contacting step.

13. The process of claim 12, wherein the regenerating step comprises contacting the hydrocarbon-immiscible quinolinium ionic liquid effluent comprising the polynuclear aromatic compound with hydrogen under hydrocracking conditions.

14. The process of claim 12, wherein the regenerating step comprises lowering a temperature of the hydrocarbon-immiscible quinolinium ionic liquid effluent to produce a crystallized polynuclear aromatic compound and a regenerated hydrocarbon-immiscible liquid; and separating the crystallized polynuclear aromatic compound from the regenerated hydrocarbon-immiscible quinolinium ionic liquid effluent.

15. The process of claim 1, wherein the hydrocarbon effluent comprises entrained hydrocarbon-immiscible quinolinium ionic liquid.

16. The process of claim 15, further comprising:
separating the entrained hydrocarbon-immiscible quinolinium ionic liquid from the hydrocarbon effluent by retaining at least a portion of the entrained hydrocarbon-immiscible quinolinium ionic liquid with a retaining material for retaining entrained hydrocarbon-immiscible quinolinium ionic liquid.

17. The process of claim 16, wherein the retaining material comprises an adsorbent selected from silica, silica gel, alumina, silica-alumina, and combinations thereof.

18. The process of claim 16, further comprising:
desorbing hydrocarbon-immiscible liquid from the adsorbent material with a desorbent.

19. The process of claim 18, further comprising:
regenerating the adsorbent material after the hydrocarbon-immiscible quinolinium ionic liquid has been desorbed from the adsorbent material.

20. The process of claim 16, further comprising:
reactivating at least a portion of the hydrocarbon-immiscible quinolinium ionic liquid that has been recovered from the retaining material.

21. The process of claim 1, wherein the polynuclear aromatic compound comprises benzoperylenes, coronenes, ovalenes, or any combination thereof.

* * * * *